United States Patent [19]

Strekowski et al.

[11] Patent Number: 5,304,647
[45] Date of Patent: Apr. 19, 1994

[54] METHOD OF PREPARATION OF HALOGENATED DIAZINES

[75] Inventors: Lucjan Strekowski, Stone Mountain; Maria Mokrosz, Decatur; Donald B. Harden, Atlanta, all of Ga.

[73] Assignee: Georgia State University Foundation, Inc., Atlanta, Ga.

[21] Appl. No.: 572,676

[22] Filed: Aug. 24, 1990

Related U.S. Application Data

[62] Division of Ser. No. 400,502, Aug. 30, 1989, Pat. No. 4,963,676, which is a division of Ser. No. 153,998, Feb. 9, 1988, Pat. No. 4,929,726.

[51] Int. Cl.$^5$ ............... C07D 239/30; C07D 237/12; C07D 239/72
[52] U.S. Cl. ........................ 544/235; 544/122; 544/237; 544/326; 544/328; 544/334; 544/283; 544/284; 544/293
[58] Field of Search ............ 544/235, 237, 326, 328, 544/334, 283, 284, 293

[56] References Cited

U.S. PATENT DOCUMENTS 4,139,622  2/1979  Rothgery et al. ............... 544/235

FOREIGN PATENT DOCUMENTS

| | | | |
|---|---|---|---|
| 0055693 | 7/1982 | European Pat. Off. | 544/235 |
| 0096657 | 12/1983 | European Pat. Off. | 544/235 |
| 366550 | 5/1958 | Fed. Rep. of Germany | 544/235 |
| 491133 | 5/1967 | Switzerland | 544/235 |
| 1303061 | 1/1973 | United Kingdom | 544/235 |
| 1385563 | 2/1975 | United Kingdom | 544/235 |

OTHER PUBLICATIONS

Elmoghayar, et al., Acta Chemica Scandinavica, B37 (1983) pp. 109–114.
Rose, et al., Acta Chemica Scandinavica, B37 (1983) pp. 613–615.
Gronowitz, et al., Acta Chemica Scandinavica, 19 (1965) pp. 1741–1748.
Harden et al, J. Org. Chem. vol. 53, pp. 4137 to 4140 (1988).
Brown, et al., Aust. J. Chem. 35, 1209–14 (1982).
Strekowski, et al., J. Org. Chem. 51, 3226 (1986).
Strekowski, et al., J. Med. Chem. 29, 1311–1315 (1986).
Strekowski, et al., J. Med. Chem. 30, 1415 (1987).
Elmoghayar, et al., Acta Chem. Scand. B 37, 160 (1983).
Strekowski, Roczniki Chemii 49, 1017 (1975).
Kauffman, Angewandte Chemie 18, 1–90 (1979).
Eguchi, et al., Chem. Abstract 91:91579p.
Merchant, et al., Chem. Abstract 94:139721v.
Brown, et al., Chem Abstract 97:216114r.
Afify, et al., Chem Abstract 106:156382u.
Solberg, et al., Chem. Abstract 110:57608y.
El-Rayyes, J. Heterocyclic Chem. 19, 415 (1982).
Hill, et al., J. Org. Chem. 36(21), 3248 (1971).
Parsons, et al., J. Chem Soc. 2016 (1966).

Primary Examiner—Floyd D. Higel
Attorney, Agent, or Firm—Kilpatrick & Cody

[57] ABSTRACT

A method of preparation of substituted halogenodiazines which are useful as intermediates in the synthesis of novel unfused heterobicyclic compounds, and the products thereof.

The reaction consists of the addition of an organolithium reagent with subsequent dehydrogenation of the addition product. The reaction takes place in one reaction vessel, without isolation of the substituted halogenodihydrodiazine intermediate. The reactions proceed at moderate temperature and in a short amount of time, which decreases the probability of side reactions and increases yield. Furthermore, the workup step is conducted under two-phase conditions to prevent hydrolysis of the substituted halogenodiazine to a substituted hydroxydiazine. The method is easy, efficient and results in a high yield of product.

The substituted halogenodiazines are used as intermediates in the synthesis of unfused heterobicyclic compounds containing an aromatic moiety, diazine, and another aromatic moiety, such as thiophene, benzene, or naphthalene, which have biological activity.

8 Claims, No Drawings

METHOD OF PREPARATION OF HALOGENATED DIAZINES

This is a divisional of U.S. Ser. No. 07/400,502, for "Novel Phthalazines and Their Method of Preparation" filed on Aug. 30, 1989, by Lucjan Strekowski, Maria Mokrosz, and Donald B. Harden, now U.S. Pat. No. 4,963,676, which is a divisional of U.S. Ser. No. 07/153,998, for "Novel Diazines and Their Method of Preparation" filed on Feb. 9, 1988, by Lucjan Strekowski, Maria Mokrosz, and Donald B. Harden, now, U.S. Pat. No. 4,929,726.

BACKGROUND OF THE INVENTION

The present invention relates to organic synthesis, and is in particular a method of preparation of substituted halogenodiazines and unfused heteropolycyclic compounds.

Halogenodiazines are important intermediate compounds in organic synthesis. Halogen atoms, F, Cl, Br and I, adjacent to ring nitrogens are easily replaced by a variety of common nucleophiles such as hydroxide ions, alkoxides, mercaptides, and amines. For example, L. Strekowski, et al., in Roczniki Chem. 49, 1017 (1975), reported a method for the synthesis of methoxy-and dimethylamino-5-bromopyrimidines in which they reacted 2,4-dichloro-5-bromopyrimidine with dimethylamine and sodium methoxide to produce the corresponding substituted pyrimidines. L. Strekowski, et al., found that the halogen atom in the C-4 position is more labile toward nucleophilic displacement than the halogen at the C-2 position, and that the reaction is regioselective.

Before the nucleophilic substitution of the halogen ortho to nitrogen in the diazine is undertaken, simple halogenodiazines can be modified by reaction with organometallic reagents. Brown, Cowden and Strekowski, in Aust. J. Chem., 35, 1209 (1982), showed that 2-chloropyrimidine could be treated with thien-2-yl lithium or thiazol-2-yl lithium to produce 2-chloro-4-(thien-2'-yl)-3,4-dihydropyrimidine and 2-chloro-4-(thiazol-2'-yl)-3,4dihydropyrimidine, respectively. The nucleophilic anion attacks the pyrimidine ring ortho to the ring nitrogen. The resulting dihydropyrimidines were oxidized by potassium permanganate ($KMnO_4$) in acetone to yield the substituted halogenopyrimidines.

The dehydrogenation of substituted halogenodihydropyrimidines with $KMnO_4$ is synthetically difficult for several reasons. First, manganese dioxide, a $KMnO_4$ reaction byproduct, is a finely dispersed solid which is difficult to remove from the reaction mixture. Dehydrogenation with $KMnO_4$ also requires the isolation of the dihydro-addition product of the organolithium reagent with halogenopyrimidine before the oxidation step. This is necessary because $KMnO_4$ is not soluble in ether solvents normally used for reactions with organolithium reagents. The solvent removal step is time consuming and contributes to a lower yield. The oxidation typically is performed at elevated temperature, resulting in further side products and lower yield. Oxidation of the dihydropyrimidine with $KMnO_4$ also requires large volumes of anhydrous acetone. For example, Brown, et al. used 1200 ml of anhydrous acetone solvent in the dehydrogenation of 4.6 grams of 2-chloro-4-(thien-2'-yl)-3,4-dihydropyrimidine. If the solvent is wet, the halogenodihydropyrimidine is hydrolyzed to the hydroxy compound, 2-hydroxy-4-(thien-2'-yl)-3,4-dihydropyrimidine. Furthermore, it is difficult to prepare large volumes of strictly anhydrous acetone.

In addition, only a small amount of product is recovered due to the synthetic difficulties involved in the two step procedure requiring the addition of an organolithium reagent and subsequent dehydrogenation of the addition product under different solvent conditions. Brown, et al. reported a yield of approximately 37% for the synthesis of 2-chloro-4-(thiazol-2'-yl)-pyrimidine using potassium permanganate as the oxidizing reagent. Similarly, S. Gronowitz and J. Roe, in Acta Chem. Scand. 19, 1741 (1965) reported yields of 37% for the two step synthesis of 4-(2'-thienyl)-5-bromopyrimidine and of 47% for 4-(2'-thienyl)-2-bromopyrimidine, prepared using potassium permanganate to dehydrogenate the organolithium addition product.

In a variation of the two step procedure to produce substituted halogenopyrimidines, Elmoghayar and coworkers (Acta Chem. Scand. B 37, 160 (1983); Acta Chem. Scand. B 37 109 (1983)) reacted 2,4-dichloro-5-halopyrimidine with a Grignard reagent in the presence of a catalyst, dichloro-[1,3-bis(diphenylphosphinopropane]nickel (II) [$NiCl_2$ (dppp)]. When alkyl Grignard reagents are used, the product is a mixture of 2,4-dialkyl-5-halopyrimidine and 2,4-dichloro-5-halo-6-alkyl-1,6-dihydropyrimidine in a ratio of 7:1 (47%:7%). When an aralkyl Grignard reagent is used, the only product recovered is 2,4-dichloro-5-halo-6-aralkyl-1,6-dihydropyrimidine, which is dehydrogenated in a separate step with 2,3-dichloro-5,6-dicyanobenzoquinone (DDQ), with an overall yield of 34%. Similarly, Rise and coworkers, Acta Chem. Scand. B 37 613 (1983), reacted 5-cyano-2-methylthiopyrimidine with a Grignard reagent to form 5-cyano-2-methylthio-4-phenyl-3,4-dihydropyrimidine, which was isolated and then dehydrogenated with DDQ in a second step to 5-cyano-2-methylthio-4-phenylpyrimidine, with a yield of 40%. 5-Cyano-4-methylthiopyrimidine was similarly prepared, with a yield of 45%.

Dihydropyrimidines can also be dehydrogenated with nitrobenzene. For example, as described by T. Kauffmann, Angew. Chem. Int. Ed. Engl. 18, 1 (1979), 4-(2'-pyridyl)-3,4-dihydropyrimidine was dehydrogenated with nitrobenzene to produce 4-(2'-pyridyl)-pyrimidine in 30% yield.

These methods of synthesis of substituted halogenopyrimidines, in which an organometallic compound is reacted with a halogenopyrimidine and the intermediate dihydro-addition product is isolated before dehydrogenation, under conditions which encourage side product formation, are difficult and inefficient.

It is therefore an object of the present invention to provide an easy, efficient method of synthesis of substituted halogenated diazines which results in a high yield of product.

It is another object of the present invention to provide a method to add a functional group to a halogenodiazine which does not hydrolyze the halogen group.

It is still another object of the present invention to provide novel substituted halogenodiazines which may be used as intermediates in organic synthesis.

It is yet another object of the present invention to provide novel unfused heteropolycyclic compounds having biological activity.

SUMMARY OF THE INVENTION

The present invention is a method of synthesizing substituted halogenodiazines which are useful as intermediates in the synthesis of novel unfused heteropolycyclic compounds, and the products thereof.

The method is easy, efficient and results in a high yield of product. The reaction consists of the addition of an organolithium reagent to a halogenodiazine with subsequent dehydrogenation of the addition product. The entire reaction takes place in one reaction vessel, without isolation of the substituted halogenodihydrodiazine intermediate. The reactions proceed at moderate temperature and in a short period of time, which decreases side reactions and increases yield. Furthermore, the recovery is conducted under two-phase conditions to prevent hydrolysis of the substituted halogenodiazine to a substituted hydroxydiazine.

The substituted halogenodiazines are used as intermediates in the synthesis of unfused heteropolycyclic compounds containing a diazine and an aromatic moiety, such as thiophene, benzene, naphthalene, furan, a diazine, pyridine or pyrrole, or a substituted aromatic.

DETAILED DESCRIPTION OF THE INVENTION

The present invention is a method of preparation of substituted halogenodiazines useful as intermediates in the synthesis of unfused heteropolycyclic compounds having biological activity.

Substituted halogenopyrimidines are useful as intermediates in the synthesis of unfused heterobicyclic compounds. Recently, Strekowski, et al., reported in the *J. Med. Chem.* 29, 1311 (1986) that N,N-dimethyl-2-[[4'-(thien-2''-yl)pyrimidin-2'-yl]thio]ethylamine and N-[2''-(dimethylamino)ethyl]-4-(thien-2'-yl)pyrimidin-2-amine amplify the effect of two anti-cancer drugs, bleomycin and phlemycin. The most active compounds are composed of at least two unfused conjugated aromatic rings and are cationic or can acquire a positive charge by protonation of a nitrogen. As a general rule, an anionic or potential anionic center in the molecule decreases activity. In 1987, Strekowski, et al., reported in *J. Med. Chem.* 30, 1415 (1987) that 2,5-bis[2'-[[2''-(dimethylamino)ethyl]thio]pyrimidin-4'-yl]thiophene, a heterotricyclic compound, also acts as an amplifier of bleomycin.

The method of synthesis of substituted halogenodiazines presented here is easy and efficient since the entire reaction takes place in one vessel using a moderate amount of solvent. The reaction is performed under moderate temperatures within a short period of time, increasing yield. Yield is also increased by minimizing hydrolysis of the halogen during the reaction by performing the recovery step under two phase conditions.

This method is a significant improvement over other methods of synthesis of substituted halogenopyrimidines requiring isolation of the addition product before dehydrogenation.

SYNTHESIS OF SUBSTITUTED HALOGENOPYRIMIDINES

Described below is the preferred method of synthesis of substituted halogenopyrimidines of the general formula

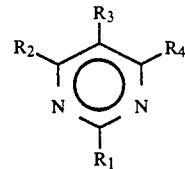

wherein: $R_1$, $R_2$, $R_3$ and $R_4$ are hydrogen, halogen, alkyl, mercaptyl, alkoxyl, alkenyl, alkynyl, aromatic or heteroaromatic groups; at least one of $R_1$, $R_2$ or $R_4$ is a halogen, and at least one of $R_1$, $R_2$ or $R_4$ is a hydrogen.

The method of the present invention is described as follows. An organolithium, or other organometallic, reagent is reacted with a halogenodiazine in an organic solvent such as diethyl ether at a temperature between about $-60°$ C. and the boiling point of the organic solvent, preferably between about $-30°$ and $-15°$ C. The reaction rate will decrease with lower temperatures and the amount of side products will increase with higher temperature. After a few minutes up to approximately one hour, the reaction is quenched with water, alcohol or an aqueous acid, preferably using approximately 1-2 molar equivalents of water dissolved in tetrahydrofuran. A quinone which undergoes facile reduction, such as 2,3-dichloro-5,6-dicyanobenzoquinone (DDQ), 2,3,5,6-tetrachlorobenzoquinone (TCQ) or 3,4,5,6-tetrachlorobenzoquinone (TCB), is then added into the same reaction vessel. The mixture is stirred, usually at room temperature. The temperature of reaction is a function of the stability of the dihydrodiazene intermediate. The hydroquinone is then removed from the reaction mixture by extraction or chromatography. The preferred method is by extraction with an aqueous solution of base, such as NaOH, LiOH, KOH, LiOH, Ba(OH)$_2$, Ca(OH)$_2$ or ammonia, where the product is recovered from the organic layer.

Examples of halogenopyrimidines (Compound 1 of Scheme 1) derivatized by this method are given in Table I, a general reaction sequence is given in Scheme 1, and the products obtained (Compound 3 of Scheme 1) are given in Table II.

TABLE I

| Starting Halogenopyrimidines (1) | | | |
|---|---|---|---|
| 1 | $R_1$ | $R_2$ | $R_3$ |
| a | Cl | H | H |
| b | Cl | Cl | H |
| c | CH$_3$S | Cl | H |
| d | Cl | Cl | Br |
| e | Br | H | H |

Scheme 1

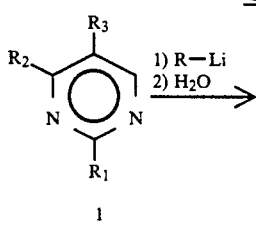

1

-continued
Scheme 1

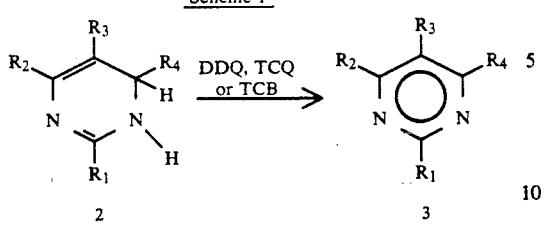

TABLE II

| | | Halopyrimidine derivatives (3) | | | |
|---|---|---|---|---|---|
| 3 | R4 | R1 | R2 | R3 | Yield % |
| a | methyl | Cl | H | H | 80 |
| b | n-butyl | Cl | H | H | 89 |
| c | phenyl | Cl | H | H | 82 |
| d | thien-2-yl | Cl | H | H | 84 |
| e | thien-3-yl | Cl | H | H | 79 |
| f | benzo[b]thiophen-2-yl | Cl | H | H | 53 |
| g | 5-(2'-hydroxyethyl)thiophen-2-yl | Cl | H | H | 25 |
| h | furan-2-yl | Cl | H | H | 63 |
| i | furan-3-yl | Cl | H | H | 57 |
| j | 1-methylpyrrol-2-yl | Cl | H | H | 27 |
| k | n-butyl | Cl | Cl | H | 93 |
| l | phenyl | Cl | Cl | H | 92 |
| m | thien-2-yl | Cl | Cl | H | 81 |
| n | thien-2-yl | CH3S | Cl | H | 84 |
| o | thien-2-yl | Cl | Cl | Br | 75 |
| p | 2,4-dichloropyrimidin-5-yl | Cl | Cl | Br | 83 |
| q | thien-2-yl | Br | H | H | 73 |

Similar transformations of 4,6-dichloropyrimidine (4) to 2-substituted-4,6-dichloropyrimidine (6) are given in Scheme 2 and Table III.

Scheme 2

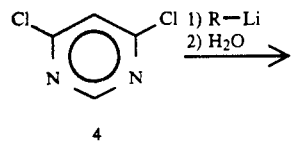

TABLE III

| | 4,6-Dichloropyrimidines 6 | |
|---|---|---|
| 6 | R | Yield % |
| a | phenyl | 68 |
| b | thien-2-yl | 77 |
| c | 4-[[2'-(dimethylamino)ethyl]thio]phenyl | 50 |
| d | benzo[b]thiophen-2-yl | 44 |

The method of the present invention can also be used to make a halophthalazine of the general formula

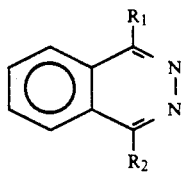

wherein:
R1 is a halogen; and
R2 is an alkyl, substituted alkyl, aromatic or substituted aromatic group.

For example, 1-chlorophthalazine (7) is easily derivatized to give a 1-chloro,4-substituted phthalazine (9) (Scheme 3 and Table IV).

Scheme 3

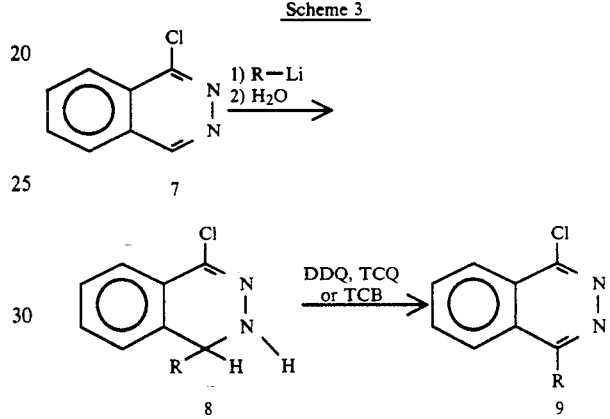

TABLE IV

| | Chlorophthalazines (9) | |
|---|---|---|
| 9 | R | Yield % |
| a | n-butyl | 87 |
| b | thien-2-yl | 57 |
| c | 2,2'-bithiophen-5-yl | 45 |

Moreover, halopyrimidines (3) with an unsubstituted 6 position undergo a similar transformation to give 2-chloro, 4-substituted, 6-substituted pyrimidines (Compounds 10–12, Schemes 4–6, Tables V–VII).

Scheme 4

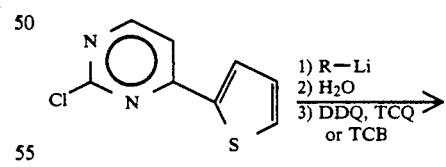

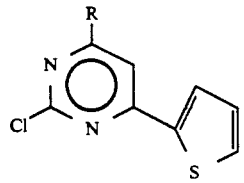

TABLE V

| 10 | R | Yield % |
|---|---|---|
| a | thien-2-yl | 69 |
| b | phenyl | 70 |

TABLE V-continued

| 10 | R | Yield % |
|---|---|---|
| c | 3-[[2'-(dimethylamino)ethyl]thio]phenyl | 68 |
| d | 4-[[2'-(dimethylamino)ethyl]thio]phenyl | 46 |
| e | benzo[b]thiophen-2-yl | 53 |

Scheme 5

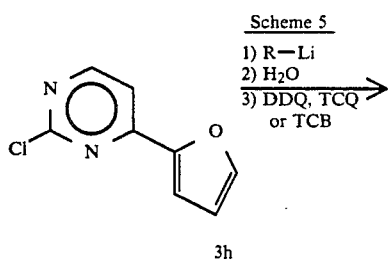

TABLE VI

| 11 | R | Yield % |
|---|---|---|
| a | benzo[b]thiophen-2-yl | 87 |
| b | 5-(2'-hydroxyethyl)thiophen-2-yl | 40 |
| c | 1-methylpyrrol-2-yl | 38 |

Scheme 6

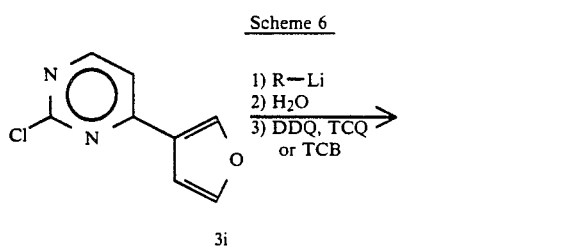

TABLE VII

| 12 | R | Yield % |
|---|---|---|
| a | benzo[b]thiophen-2-yl | 85 |

More specifically, in a typical preparation, a solution of a halogenodiazine in diethyl ether is added dropwise to a solution of an organolithium reagent in diethyl ether at a temperature between about −30° to −15° C. Alternatively, the lithium reagent can be added to the halogenodiazine. The reaction mixture is stirred at a temperature between about −30° and 0° C. for 1 h and then quenched with water (approximately 1-2 molar equivalents) dissolved in tetrahydrofuran. The quenched mixture is treated with a solution of DDQ, TCB or TCQ in tetrahydrofuran or other suitable solvent, and stirred. Unstable intermediate dihydro products, such as substituted dihydro-5-bromopyrimidines, are treated with a quinone at −15° C. with stirring for 1 h, and then briefly at room temperature. The more stable intermediate products, such as the substituted dihydro-5-chloropyrimidines, are aromatized at room temperature within 15 min. 4,6-Dichloropyrimidine (4) is reacted to yield 6 by stirring of the mixture with a quinone for 1 hour at room temperature. During these reactions, intermediate dihydrodiazines 2, 5, and 8, without isolation, are dehydrogenated to aromatic diazines, and the quinone is hydrogenated to a hydroquinone. In order to remove the hydroquinone, the reaction mixture is shaken briefly (2 min) with a cold, 10% aqueous solution of NaOH. The organic layer containing the aromatic halogenodiazine is separated and dried. The product is purified by chromatography and/or crystallization from hexane or other hydrocarbon solvents.

In the preferred method, the reaction with the quinone is conducted under two-phase conditions, with organic and aqueous phases. The product is present in the organic solution, while the hydroquinone is extracted to the basic aqueous solution. The two-phase conditions prevent hydrolysis of the halogenodiazine to a hydroxydiazine.

The yields of products 3, 6, and 9–12 are given for the reactions with DDQ in Tables II-VII. Similar results are obtained if TCQ or TCB is substituted for DDQ. The latter two quinones are less soluble in tetrahydrofuran than DDQ and, therefore, a larger volume of the solvent is required. However, the reactions proceed with only slightly lower yields if the quinones are introduced to the reaction mixtures in the form of a slurry with tetrahydrofuran or diethyl ether.

The following non-limiting examples provide detailed procedures for the synthesis of the substituted halogenopyrimidines.

2-Chloro-4-(thien-2'-yl)pyrimidine (3d)

A solution of n-butyllithium (2M, 52 mmol) in hexanes was added to a solution of thiophene (60–90 mmol) in dry ethyl ether (200 mL) at 0° C. under a nitrogen atmosphere. After 30 min the resultant 2-thienyllithium reagent was cooled to −30° C. and treated with a suspension of 2-chloropyrimidine (50 mmol) in ethyl ether (75 mL). The mixture was stirred at −30° C. for 30 min, then at 0° C. for 30 min, quenched with water (1 mL) at 0° C., treated with a solution of DDQ (52 mmol) in tetrahydrofuran (40 mL), stirred at room temperature for 5 min, treated at 0° C. with a cold aqueous solution of sodium hydroxide (10%, 25 mL), and stirred at 0° C. for 5 min. The organic layer was dried (Na₂SO₄) decolorized with charcoal or silica gel, and concentrated to give a crystalline residue. Crystallization from toluene-hexanes (4:1) yielded pale yellow needles of 2-chloro-4-(thien-2'-yl)pyrimidine (84%); m.p. 132°-134° C.

$^1$H-NMR (CDCl₃) δ: 7.28(t, 1H), 7.93(d, H), 8.00(d, 1H), 8.13(d, 1H), 8.72 ppm (d, 1H).

Compounds 3a-c, 3e-n, 3q, 10a-c, 11a-c, and 12a were prepared from the respective lithium reagents and chloropyrimidines in a similar manner. Detailed procedures for 3o, 3p and 6b are provided below.

5-Bromo-2,4-dichloro-6-(thien-2'-yl)pyrimidine (3o)

A solution of 2-thienyllithium in diethyl ether was prepared as described above, cooled to −45° C., and treated dropwise (5 min.) with a solution of 5-bromo-2,4-dichloropyrimidine (50 mmol) in ethyl ether (20 mL). The mixture was stirred at −40° C. for 1 h, quenched at −20° C. with a mixture of acetic acid (2.5 mL) and methanol (2.0 mL), treated at −20° C. with a solution of DDQ (52 mmol) in tetrahydrofuran (100 mL), and warmed to 0° C. within 1 h with continuing stirring. The stirred mixture was treated at 0° C. with ethyl ether (100 mL) and then with a cold aqueous solution of sodium hydroxide (10%, 25 mL). The organic layer was dried ($Na_2SO_4$), decolorized with charcoal or silica gel, and concentrated to give a crystalline residue. Crystallization from dichloromethane-hexanes (1:1) yielded needles of 5-Bromo-2,4-dichlor(thien-2'-yl)pyrimidine (75%), m.p. 123°–124° C.

$^1$H-NMR ($CDCl_3$) δ: 7.13(t, 1H), 7.63(d, 1H), 8.73 ppm (d, 1H).

5-Bromo-2,2',4',6-tetrachloro-4,5'-bipyrimidine (3p).

A solution of n-butyllithium (2M, 25 mmol) in hexanes was added dropwise within 5 min to a solution of 5-bromo-2,4-dichloropyrimidine (52 mmol) in dry ethyl ether (250 mL), maintained at −70° C. and stirred under a nitrogen atmosphere. The mixture containing a yellow precipitate was then stirred at −45° C. for 30 min, quenched at −45° C. with a mixture of acetic acid (1.5 mL) and methanol (1.0 mL), stirred at −45° C. until the yellow precipitate disappeared (5–10 min), and treated at −45° C. with a solution of DDQ (52 mmol) in tetrahydrofuran (100 mL). Stirring was then continued at 0° C. for 15 min. Work-up, as described above for 5-Bromo-2,4-dichloro-6-(thien-2'-yl)pyrimidine, and followed by crystallization of the residue from dichloromethane-hexanes (3:10), yielded 5-bromo-2,2',4',6-tetrachloro-4,5'-bipyrimidine (83%) as white crystals; m.p. 136°–138° C.

$^1$H-NMR ($CDCl_3$) δ: 8.66 ppm (s).

4,6-Dichloro-2-(thien-2'-yl)pyrimidine (6b)

A mixture of 2-thienyllithium (prepared from 52 mmol of n-butyllithium, as described for 3d) and 4,6-dichloropyrimidine (50 mmol) in ethyl ether (80 mL) was allowed to react at −15° C. for 1 h, quenched at −15° C. with a mixture of acetic acid (2.5 mL) and water (1 mL), and then treated at 0° C. with a solution of DDQ (50 mmol) in tetrahydrofuran (150 mL), and stirred at room temperature for 1 h. Work-up as described above and followed by crystallization of the residue from dichloromethane-hexanes (1:3) gave yellow needles of 4,6-dichloro-2(thien-2'-yl)pyrimidine (77%); m.p. 129°–130° C.

Compounds 6a and 6c,d were prepared from 4,6-dichloropyrimidine and the appropriate lithium reagents, and 9a–c were prepared from 1-chlorophthalazine and the appropriate lithium reagents by application of essentially the same procedure.

The method of the present invention can be used to produce a quinazoline of the general formula

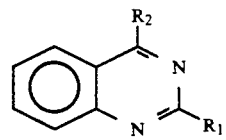

wherein: $R_1$ is a halogen and the $R_2$ group is an aromatic or heteroaromatic or substituted aromatic or heteroaromatic group.

In this method, 2,4-dichloroquinazoline (13) is reacted with lithium reagents (Scheme 7 and Table VIII). As discussed in the background of the invention, 2,4-dichloropyrimidines undergo a regioselective substitution of the chlorine atom at position 4. This has also been observed in the reaction of 13 with organolithium reagents. Products 14 are produced preferentially when equimolar amounts of 13 and lithium compounds are used in the reaction.

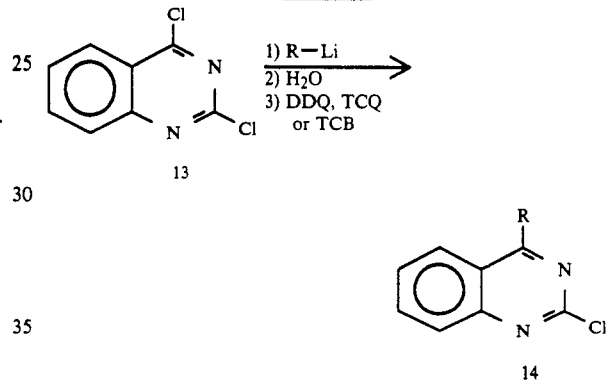

Scheme 7

TABLE VIII

| | 2-Chloroquinazolines | |
|---|---|---|
| | R | Yield % |
| a | phenyl | 69 |
| b | thien-2-yl | 76 |
| c | benzo[b]thiophen-2-yl | 55 |
| d | naphth-2-yl | 40 |

The method of the present invention can also be used to make 4-chloro-2,6-di (aromatic)pyrimidines of the following general formula wherein $R_1$ and $R_2$ are aromatic or heteroaromatic and substituted aromatic or heteroaromatic groups.

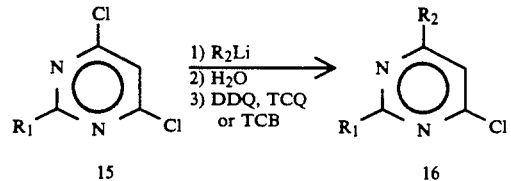

Scheme 8

TABLE IX

| 4-Chloro-2,6-di(substituted)pyrimidines | |
|---|---|
| R | yield % |
| thien-2'-yl | 62 |

The following non-limiting examples provide detailed procedures for the synthesis of the substituted halogenoquinazolines such as 14 and substituted halogenopyrimidines such as 16.

2-Chloro-4-(napth-2′-yl)quinazoline (14d)

2-Bromonaphthalene (9.7 mmol) in diethyl ether (10 mL) was treated dropwise at 0° C. with n-butyllithium (2M, 9.7 mmol). The resultant 2-naphthyllithium reagent was added dropwise at 0° C. to a solution of 2,4-dichloroquinazoline (9.3 mmol) in diethyl ether (50 mL). The mixture was stirred at 0° C. for 1 h, and then quenched with water (0.5 mL). The ether was dried ($Na_2SO_4$), treated with charcoal or silica gel, and evaporated to give a solid residue. Short-path column chromatography (silica gel/dichloromethane with hexanes) and followed by crystallization from hexanes-toluene (1:1) yielded white crystals of 2-chloro-4-(napth-2′-yl)quinazoline (40%); m.p. 158°-160° C.

$^1$H-NMR (CDCl$_3$) δ: 7.3-8.3 ppm (m).

Other compounds were prepared in a similar manner using the appropriate lithium reagents.

4-Chloro-2,6-di (thien-2′-yl)pyrimidine

A solution of 2-thienyllithium was prepared from thiophene (15 mmol) in diethyl ether (20 mL) and n-butyllithium in hexanes (2M, 11 mmol). The lithium reagent was added dropwise at room temperature to a solution of 4,6-dichloro-2-(thien-2′-yl)pyrimidine (10 mmol) in diethyl ether (150 mL) maintained under a nitrogen atmosphere and stirred. The mixture was stirred at room temperature for 1.5 h and then quenched with water (1 mL). The ether was dried ($Na_2SO_4$), treated with charcoal or silica gel, and evaporated to give a crystalline residue. Crystallization from hexanes gave 4-chloro-2,6-di(thien-2′-yl)pyrimidine (62%); m.p. 128°-130° C. $^1$H-NMR (CDCl$_3$) δ: 7.12 (m, 2H), 7.29(s,1H, 7.50(m, 2H), 7.75(m, 1H), 8.03(m, 1H).

New compounds 3, 6, 9-12, 14 and 16 are intermediate products for the preparation of unfused heteropolycyclic derivatives having biological activities including activity against the retrovirus responsible for acquired immune deficiency syndrome (AIDS).

DERIVATIZATION OF UNFUSED HETEROPOLYCYCLIC COMPOUNDS

In the second step of the synthetic scheme to produce derivatized unfused heteropolycyclic compounds, specifically heterobicyclic and heterotricyclic compounds, the halogen atoms adjacent to the diazine ring nitrogens are replaced by one of a variety of common groups such as the hydroxide ion, alkoxides, mercaptides, and amines. Examples of useful nucleophiles are 1-(2-mercaptoethyl)-4-methylpiperazine, morpholine, 2-hydroxyethylamine, N,N-dimethyl-(2-mercaptoethyl)-amine, N,N-dimethylethylenediamine, and N,N-dimethyl-1,3-propanediamine.

The general reaction scheme in which intermediates 3, 6, 9-12, 14 and 16 are converted into unfused heteropolyaromatic compounds that may have biological application is illustrated as follows: The chloro derivative was treated with a 50-fold excess of the appropriate amine. The mixture was heated at 70°-80° C. for one hour and the amine recovered by distillation. The oily residue was treated with a few drops of 5% NaOH and extracted with ether. The ether solution was dried over $Na_2SO_4$, evaporated, and the product purified by flash chromatography on $SiO_2$. Further purification was done via crystallization from a toluenehexane mixture.

The following are non-limiting examples of new classes of unfused heteropolyaromatic compounds.

A substituted phthalazine of the general formula

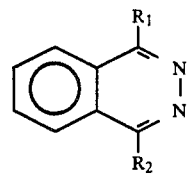

wherein:
$R_1$ is —NHX, —NX$_2$, —OX, or —SX, where X is H or an organic radical and
$R_2$ is an aromatic or substituted aromatic.
A specific example is $R_1=$

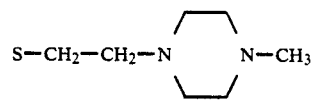

and $R_2=$2-benzothiophenyl, 2-napthyl, or phenyl.

Aromatic groups include furanyl, thienyl, benzyl, napthyl, and pyridyl. For example, aromatic groups can be substituted with alkoxy, alkylthio, dialkylamino, and hydrocarbon groups. If the substitution contains an —OH or —SH, the quantity and nature of the organometallic reagent should be adjusted as necessary for reaction with the —OH or —SH.

A substituted quinazoline of the general formula

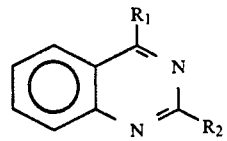

wherein:
$R_1$ is —NHX, —NX$_2$, —OX, or —SX, where X is H or an organic radical and
$R_2$ is any aromatic or substituted aromatic.

A substituted quinazoline of the general formula

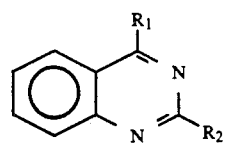

wherein:
$R_1$ is any aromatic or substituted aromatic and
$R_2$ is —NHX, —NX$_2$, —OX, or —SX, where X is H or an organic radical.

A specific example is $R_1=$2-benzothiophenyl and $R_2=$—NH—CH$_2$—CH$_2$—N(CH$_3$)$_2$. These compounds can be made in good yield from 2-halo-4-substituted quinazolines, which are prepared through the reaction of 2-halo quinazoline with an organolithium reagent followed by aromatization of the intermediate.

A pyrimidine of the general structure

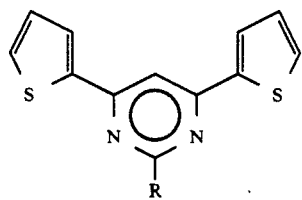

wherein: R is —NHX, —NX₂, —OX, or —SX, where X is H or an organic radical.

Specific examples of R are —S—CH₂—CH₂—N(CH₃)₂; —NH—CH₂—CH₂—N(CH₃)₂;

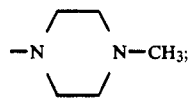

—NH—CH₂—CH₂—CH₂—N(CH₃)—CH₂—CH₂—CH₂—NH₂;

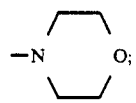

—NH—CH₂—CH₂—OH; —N(CH₂—CH₂—OH)₂; and —O—CH₂—CH₂—N(CH₂—CH₂—OH)₂.

A pyrimidine of the general formula

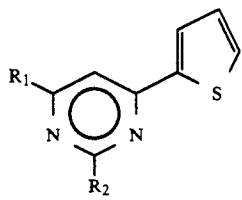

wherein:
R₂ is —NHX, —NX₂, —OX, or —SX, where X is H or an organic radical and
R₁ is any aromatic or substituted aromatic.
Specific examples are R₂=

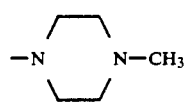

and R₁=phenyl or 2-napthyl; and R₂ is —S(CH₂)₂N(CH₃)₂ and R₁ is N-methylpyrrol-2-yl.

A pyrimidine of the general formula

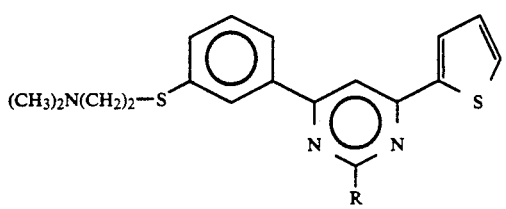

wherein: R is —NHX, —NX₂, —OX, or —SX, where X is H or an organic radical, such as —S—CH₂—CH₂—N(CH₃)₂, —NH—CH₂—CH₂—N(CH₃)₂, or —NH—CH₂—CH₂—CH₂—N(CH₃)—CH₂—CH₂—CH₂—NH₂, A pyrimidine of the general formula

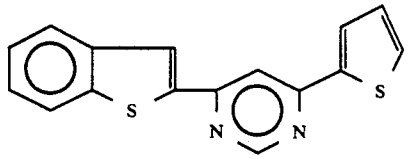

wherein R is —NHX, —NX₂, —OX, or —SX, where X is H or an organic radical, such as

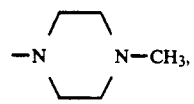

—NH—CH₂—CH₂—N(CH₃)₂, —O—CH₂—CH₂—N(CH₂—CH₂—OH)₂, —N(CH₂CH₂OH)₂ or —NH—CH₂—CH₂—CH₂—N(CH₃)—CH₂—CH₂—CH₂—NH₂.

A substituted pyrimidine of the general formula

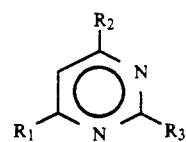

wherein R₁ and R₂ are aromatic or substituted aromatic groups and R₃ is —NHX, —NX₂, —OX, or —SX, where X is H or an organic radical.

A substituted pyrimidine of the general formula

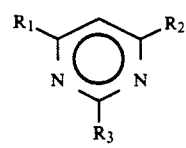

wherein R₁ and R₂ are —NHX, —NX₂, —OX, or —SX, where X is H or an organic radical and R₃ is aromatic or substituted aromatic groups.

A substituted pyrimidine of the general formula

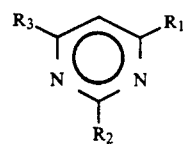

wherein R₁ and R₂ are aromatic or substituted aromatic groups and R₃ is —NHX, —NX₂, —OX, or —SX, where X is H or an organic radical.

The method of the present invention is further described by the following non-limiting examples.

4-Methyl-1-[4',6'-di(thien-2''-yl)pyrimdin-2'-yl]piperazine

A mixture of N-methylpiperazine (10 mL) and 2-chloro-4,6-di(thien-2'-yl)pyrimidine (10 mmol) was heated at 70° C. for 1 h. The excess of amine was recovered by distillation and the residue was treated with aqueous sodium hydroxide (1M, 10 mL). The mixture was extracted with ethyl ether. The extract was dried ($Na_2SO_4$), decolorized with charcoal or silica gel, and evaporated to give a crystalline residue. Crystallization from toluene-hexanes (2:8) gave 4-methyl-1-[4',6'-di(thien-2''-yl)pyrimidin-2'-yl]piperazine (86%); m.p. 132°–134° C.

$^1$H-NMR (CDCl$_3$) δ:2.33(s, 3H), 2.50(t, 4H), 3.93(t, 4H, 7.10(m, 3H), 7.43(d, 2H), 7.70 ppm (d, 2H).

A warm solution of 4-methyl-1-[4',6'-di (thien-2''-yl)pyrimidin-2'-yl]piperazine in ethanol was treated with a mixture of aqueous hydrobromic acid (48%) and ethanol (ca 10 mmol of HBr). Refrigeration gave a hydrobromide salt of 4-methyl-1-[4',6'-di (thien-2''-yl)pyrimidin-2'-yl]piperazine (4-methyl-1-[4',6'-di (thien-2''-yl)pyrimidin-2'-yl]piperazine.HBr.½H$_2$O); m.p. 302°–303° C.

N,N-Dimethyl-2-[[4',6'-di (thien-2''-yl)pyrimidin-2'-yl]thio]ethylamine

2-Chloro-4,6-di (thien-2'-yl)pyrimidine (10 mmol), 2-dimethylaminoethanethiol hydrochloride (10 mmol), and ethanol (60 mL) containing sodium hydroxide (20 mmol) were heated under reflux for 2 h. The residue from evaporation was extracted with ether-toluene (4:1). The extract was evaporated and the residue was crystallized from methanol to give N,N-dimethyl-2-[[4',6'-di (thien-2''-yl)pyrimidin-2'-yl]thio]ethylamine (85%); m.p. 108°–109° C.

$^1$H-NMR (CDCl$_3$) δ:2.33(s, 6H), 2.75(m, 2H), 3.30(m, 2H), 7.08(2d, 2H), 7.34(s, 1H), 7.40(2d, 2H), 7.70 ppm (2d, 2H).

N,N-Bis(2'-hydroxyethyl)-2-[[4'',6''-di (thien-2'''-yl)pyrimidin-2''-yl]oxy]ethylamine Dry triethanolamine (10 mL) in toluene (20 mL) was treated with sodium hydride (2.1 mmol) under a nitrogen atmosphere, and the resulting mixture was stirred until evolution of hydrogen ceased. 2-chloro-4,6-di (thien-2'-yl)pyrimidine (2 mmol) was then added and the mixture was heated at 100° C. for 1 h. The excess of triethanolamine was recovered by distillation under reduced pressure and the residue was diluted with aqueous sodium hydroxide (1M, 5 mL) and extracted with ether. The dried extract was evaporated and the resulting oil was dissolved in ethanol (20 mL) and then treated with a mixture of hydrobromic acid (48%, 2 mmol) and ethanol (5 mL). The hydrobromide of N,N-bis(2'-hydroxyethyl)-2-[[4'',6''-di (thien-2'''-yl)pyrimidin-2''-yl]oxy]ethylamine was precipitated by the addition of ethyl ether. Crystallization from ethanol-ether (9:1) gave N,N-bis(2'-hydroxyethyl)-2-[[4'',6''-di (thien-2'''-yl)pyrimidin-2''-yl]oxy]ethylamine.HBr (62%); m.p. 138°–140° C.

$^1$H-NMR of the free base (CDCl$_3$) δ:2.80(m, 6H), 3.63(t, 4H), 4.08(s, 2H), 4.48(t, 2H), 7.10(m+s, 3H), 7.36(m, 2H), 7.68 ppm (m, 2H).

Utilizing the steps described above, the compounds listed in Tables IX–XVI were prepared.

TABLE IX
Substituted quinazolines

| Molecular Formula | Mol. Weight | Compound Name |
|---|---|---|
| $C_{21}N_{24}N_4S.2HBr$ | 526.3 | 1-[2'[(4''-Phenylquinazolin-2''-yl)thio]ethyl]-4-methylpiperazine |
| $C_{25}H_{26}N_4S.2HBr$ | 576.4 | 1-[2'-[[4''-(Naphth-2' ''-yl)quinazolin-2''-yl]thio]ethyl]-4-methylpiperazine |
| $C_{23}H_{24}N_4S_2.2HBr$ | 600.4 | 1-[2'-[[4''-(Benzothiophen-2' ''-yl)quinazolin-2''-yl]thio]ethyl]-4-methylpiperazine |

TABLE X
Substituted Phthalazines.

| Molecular Formula | Mol. Weight | Compound Name |
|---|---|---|
| $C_{23}H_{24}N_4S_2.2HBr.H_2O$ | 600.4 | 1-[2'-[[4''-(Benzo[b]thiophen-2' ''-yl)phthalazin-1''-yl]thio]ethyl]-4-methylpiperazine |
| $C_{25}H_{26}N_4S.2HBr$ | 576.4 | 1-Methyl-4-[2'-[[4''-(naphth-2' ''-yl)phthalazin-1''-yl]thio]ethyl]piperazine |

TABLE XI
Substituted Pyrimidines.

| Molecular Formula | Mol. Weight | Compound Name |
|---|---|---|
| $C_{16}H_{15}N_3OS_2$ | 329.4 | 2-Morpholino-4,6-bis(thien-2'-Yl)pyrimidine |
| $C_{14}H_{13}N_3OS_2$ | 303.4 | N-(2'-Hydroxyethyl)-4,6-bis(thien-2''-yl)pyrimidin-2-amine |
| $C_{16}H_{17}N_3O_2S_2$ | 347.5 | N,N-Bis(2'-hydroxyethyl)-4,6-bis(thien-2''-yl)pyrimidin-2-amine |
| $C_{18}H_{21}N_3O_3S_2.HBr$ | 472.4 | N,N-Bis(2'-hydroxyethyl)-2-[[4'',6''-bis(thien-yl)pyrimidin-2''-yl]oxy]ethylamine |
| $C_{16}H_{17}N_3A_3$ | 347.5 | N,N-Dimethyl-2-[[4',6'-bis(thio]n-2''-yl)pyrimidin-2'-yl]thien]ethylamine |
| $C_{16}H_{18}N_4S_2.2HBr$ | 429.3 | N-[2''-(Dimethylamino)ethyl]-4,6-bis(thien-2'-yl)pyrimidin-2-amine |
| $C_{19}H_{25}N_5S_2$ | 387.6 | N-[3''-[3' '' Aminopropyl)methylamino]propyl]-4,6-bis(thien-2'-yl)pyrimidin-2-amine |
| $C_{17}H_{18}N_4S_2$ | 342.5 | 4-Methyl-1-[4',6'-bis(thien-2''-yl)pyrimidin-2'-yl]piperazine |

TABLE XII
Substituted Pyrimidines.

| Molecular Formula | Mol. Weight | Compound Name |
|---|---|---|
| $C_{17}H_{20}N_4S_2.HBr$ | 425.4 | N,N-Dimethyl-2-[[4'-(1''methypyrrol-2''-yl)-6'-(thien-2' ' '-yl)pyrimidin-2'-yl]thio]ethylamine |
| $C_{17}H_{20}N_4S$ | 312.4 | 1-Methyl-4-[4'-phenyl-6'-(thien-2''yl)pyrimidin-2'-yl]piperazine 1-Methyl-4[4'-(naphth-2''-yl)-6'-(thien-2' ' '-yl)pyrimidin-2'-yl]piperazine |

TABLE XIII

Substituted Quinazoline.

| Molecular Formula | Mol. Weight | Compound Name |
|---|---|---|
| $C_{20}H_{20}N_4S$ | | N-[2''-(Dimethylamino)ethyl]-4-benzo[b]thiophen-2'-ylquinazolin-2-amine |

TABLE XIV

Substituted Pyrimidines.

| Molecular Formula | Mol. Weight | Compound Name |
|---|---|---|
| $C_{22}H_{28}N_4S_3 \cdot 2HBr$ | 606.5 | 2-[[2''''(Dimethylamino)ethyl]thio]-4-[[2''-(dimethylamino)ethyl]thio]phenyl]-6-(thien-2'''-yl)pyrimidine |
| | | N-[2''''-(Dimethylamino)ethyl]-4-[3'-[[2''-(dimethylamino)ethyl]thiophenyl]-6-(thien-2'''-yl)pyrimidin-2-amine |
| | | N-[3'''-](3'''''-Aminopropyl)methylamino]propyl]-4-[3'-[[2''-(dimethylamino)ethyl]thio]phenyl]-6-(thien-2'''-yl)pyrimidin-2-amine |

TABLE XV

Substituted Pyrimidines.

| Molecular Formula | Mol. Weight | Compound Name |
|---|---|---|
| $C_{22}H_{29}N_5S_2$ | 395.5 | N-[2'''-(Dimethylamino)ethyl]-4-[4'-[[2''-(dimethylamino)ethyl]thio]phenyl]-6-(thien-2'''-yl)pyrimidin-2-amine |

TABLE XVI

Substituted Pyrimidines.

| Molecular Formula | Mol. Weight | Compound Name |
|---|---|---|
| $C_{21}H_{20}N_4S_2 \cdot 2HCl$ | | 1-[4'-(Benzo[b]thiophen-2''-yl)-6-(thien-2''' yl)-yl)pyrimidin-2'-yl]-4-methylpiperazine |
| $C_{20}H_{20}N_4S_2 \cdot 2HBr$ $\frac{1}{2}H_2O$ | 551.3 | N-[2'''-(Dimethylamino)ethyl]-4-(benzo[b]thiophen-2'-yl)-6-(thien-2''-yl)pyrimidin-2-amine |
| $C_{22}H_{23}N_3O_3S_2 \cdot$ HBr | 522.5 | N,N-Bis(2''''-hydroxyethyl)-2-[[4'-(benzo[b]thiophen-2''-yl)-6'-(thien-2'''-yl)pyrimidin-2'-yl]oxyl]ethylamine |
| $C_{20}H_{19}N_3O_2S_2$ | 413.5 | N,N-Bis(2''''-hydroxyethyl)-4-(benzo[b]thiophen-2'-yl)-6-(thien-2''-yl)pyrimidin-2-amine |
| $C_{23}H_{27}N_5S_2$ | 437.6 | N-[3''''-Aminopropyl)methylamino]propyl]-4-(benzo[b]thiophen-2'-yl)-6-(thien-2''-yl)pyrimidin-2-amine |

The unfused heteropolycyclic compounds interacted with nucleic acids to enhance the reaction rate of known anti-cancer drugs. Activity in some cases can be correlated with structure to predict the type and strength of activity.

This invention has been described with reference to its preferred embodiments. Variations and modifications of the method of synthesizing substituted halopyrimidines, along with the novel substituted halogenodizines and unfused heterobicyclic compounds described herein, will be obvious to those with ordinary skill in the art. It is intended that all of these variations and modifications be included within the scope of the appended claims.

We claim:

1. A method of modifying a halogenated aromatic 1,2- or 1,3-diazine, comprising:
   reacting the halogenated diazine with an organolithium reagent in an organic solvent to form an addition product;
   quenching the reaction with a compound selected from the group consisting of water, alcohol, and aqueous acid solutions;
   adding a quinone to dehydrogenate the addition product without prior isolation of the addition product;
   removing the hydroquinone formed during dehydrogenation of the addition product; and
   recovering the resulting product.

2. The method of claim 1 wherein the reaction is quenched with between approximately 1 and 2 molar equivalents of water.

3. The method of claim 2 wherein the organolithium reagent is reacted with the halogenated diazine at a temperature between approximately −30 degrees C. and −15 degrees C.

4. The method of claim 3 wherein the addition product is dehydrogenated at approximately room temperature for up to one hour.

5. The method of claim 1 wherein the hydroquinone is extracted with an aqueous solution having a pH greater than about 9 and the halogenated diazine is recovered from the organic layer.

6. The method of claim 1 wherein the halogen atoms adjacent to the diazine ring nitrogens of the recovered substituted halogenated diazine are reacted with a nucleophile.

7. The method of claim 6 wherein the halogen atoms are replaced by reaction with a compound selected from the group consisting of hydroxide ion, alkoxide, mercaptides, and amines.

8. The method of claim 7 wherein the halogen atoms are replaced by reaction with a nucleophile selected from the group consisting of 1-(2-mercaptoethyl)-4-methylpiperazine, morpholine, 2-hydroxyethylamine, dimethyl(-2-mercaptoethyl)amine, N,N-dimethylethylenediamine, and dimethyl-(3-aminopropyl)amine.

* * * * *